(12) United States Patent
Korte et al.

(10) Patent No.: US 7,582,677 B2
(45) Date of Patent: Sep. 1, 2009

(54) LIGNAN FORMULATIONS

(75) Inventors: Helena Korte, Turku (FI); Veli-Matti Lehtola, Turku (FI); Mikko Unkila, Littoinen (FI); Mervi Hiilovaara-Teijo, Riihikoski (FI); Markku Ahotupa, Turku (FI)

(73) Assignee: Hormos Medical Corp., Turku (FI)

( * ) Notice: Subject to any disclaimer, the term of this patent is extended or adjusted under 35 U.S.C. 154(b) by 727 days.

(21) Appl. No.: 10/513,218

(22) PCT Filed: May 15, 2003

(86) PCT No.: PCT/FI03/00375

§ 371 (c)(1),
(2), (4) Date: Nov. 3, 2004

(87) PCT Pub. No.: WO04/000304

PCT Pub. Date: Dec. 31, 2003

(65) Prior Publication Data

US 2005/0169947 A1    Aug. 4, 2005

(30) Foreign Application Priority Data

Jun. 19, 2002    (FI) .................................. 20021184

(51) Int. Cl.
*A61K 31/34* (2006.01)
(52) U.S. Cl. .................. 514/461; 514/844; 514/947
(58) Field of Classification Search .................. 514/718, 514/731, 754, 461, 844, 947; 424/401
See application file for complete search history.

(56) References Cited

U.S. PATENT DOCUMENTS

| | | | | |
|---|---|---|---|---|
| 4,708,964 A | 11/1987 | Allen | ......................... | 514/533 |
| 5,276,060 A | 1/1994 | Neiss et al. | .................. | 514/731 |
| 6,271,257 B1 * | 8/2001 | Mutanen | ...................... | 514/461 |
| 6,689,809 B2 * | 2/2004 | Ahotupa et al. | ............. | 514/473 |

FOREIGN PATENT DOCUMENTS

| | | |
|---|---|---|
| EP | 0 297 733 | 1/1989 |
| JP | 6-016525 | 1/1994 |
| JP | 9-013031 | 1/1997 |
| JP | 9-095417 | 4/1997 |
| JP | 10-279432 | 10/1998 |
| JP | 10-279461 | 10/1998 |
| JP | 10-279462 | 10/1998 |
| JP | 10-279485 | 10/1998 |
| JP | 11-255639 | 9/1999 |
| WO | WO 88/03800 | 6/1988 |
| WO | WO 98/21946 | 5/1998 |
| WO | WO 00/59946 | 10/2000 |
| WO | WO 01/03687 | 1/2001 |
| WO | WO 01/08651 | 2/2001 |
| WO | WO 01/08652 | 2/2001 |

OTHER PUBLICATIONS

Cabral et al., "Effects of Some Lignans and Neolignans on the Development and Excretion of Rhodnius Prolixus," 71 *Fitoterapia* 1-9 (Feb. 2000) (Abstract).
Ekman, "Analysis of Lignans in Norway Spruce by Combined Gas Chromatography—Mass Spectrometry," 30 *Holzforschung* 79-85 (1976).
Ito Ryuhei, "Antioxidant," JP 2000129256 Patent Abstracts of Japan Publication (May 9, 2000).
Oikarinen et al., Chemopreventive Activity of Crude Hydroxymatairesinol (HMR) Extract in Apec$^{Min}$ Mice, 161 *Cancer Letters* 253-258 (2000).
Saarinen et al., "Hydroxymatairesinol, a Novel Enterolactone Precursor With Antitumor Properties From Coniferous Tree (*Picea abies*)," 36 *Nutrition and Cance* 207-216 (2000).
Midori et al., "Anti-Tumor-Promoting Activity of Lignans from the Aerial Part of Saussurea Medusa," 158 *Cancer Letters* 53-59 (Sep. 2000) (Abstract).
Prieto et al., "Diphyllin Acetylapioside, a 5-lipoxygenase Inhibitor from Haplophyllum Hispanicum," 137 *Chemical Abstracts* 304484 (2002).
Mori et al., "Lignan Glycosides in Germinating Sesame Seeds as Anti-Aging Cosmetic Raw Materials," 136 *Chemical Abstracts* 299429 (2002).

\* cited by examiner

*Primary Examiner*—Taylor Victor Oh
(74) *Attorney, Agent, or Firm*—James C. Lydon

(57) ABSTRACT

A topical formulation which includes a lignan or lignan ester in a dermatologically acceptable vehicle. The formulation can be either a cosmetic formulation or a pharmaceutical formulation.

3 Claims, No Drawings

LIGNAN FORMULATIONS

This application is a U.S. National Stage of International application PCT/FI2003/000375, filed May 15, 2003.

FIELD OF THE INVENTION

This invention relates to topical formulations comprising lignans or lignan esters, either as active ingredients to improve the health and/or physical appearance of the skin, or as preservatives or stabilizers for other active ingredients or vehicles in topical formulations.

BACKGROUND OF THE INVENTION

The publications and other materials used herein to illuminate the background of the invention, and in particular, cases to provide additional details respecting the practice, are incorporated by reference.

Lignans are phenolic-compounds widely distributed in plants. They can be found in different parts (roots, leafs, stem, seeds, fruits) but mainly in small amounts. In many sources (seeds, fruits), lignans are found as glycosidic conjugates associated with fiber component of plants. The most common dietary sources of mammalian lignan precursors are unrefined grain products. The highest concentrations in edible plants have been found in flaxseed, followed by unrefined grain products, particularly rye.

Considerable amounts of lignans are also found in coniferous trees. The type of lignans differs in different species and the amounts of lignans vary in different parts of the trees. The typical lignans in heartwood of Norway spruce (Picea abies) are hydroxymatairesinol (HMR), alpha-conidendrin, alpha-conidendric acid, matairesinol, isolariciresinol, secoisolariciresinol, liovil, picearesinol, lariciresinol and pinoresinol (Ekman R: Distribution of lignans in Norway spruce. Acta Academiae Aboensis, Ser B, 39:1-6, 1979).

The far most abundant single component of lignans in spruce is HMR, about 60 percent of total lignans, which occurs mainly in unconjugated free form. Plant lignans such as hydroxymatairesinol, matairesinol, lariciresinol and secoisolariciresinol, are converted by gut microflora to mammalian lignans, enterolactone or enterodiol. The mammalian lignans can also be manufactured synthetically (M B Groen and J Leemhius, Tetrahedron Letters 21, 5043, 1980).

Lignans are known to possess beneficial effects on human health. The health benefits obtained with lignan rich diet are, for example, decreased risk for various cancers and cardiovascular diseases (Adlercreutz (1998) Phytoestrogens and human health, In: Reproductive and Developmental Toxicology (edited by Korach, K.). pp. 299-371, Marcel & Dekker, N.Y.).

Lignans, such as hydroxymatairesinol, WO 00/59946, have also been reported to inhibit lipid peroxidation and LDL oxidation and thus be useful as antioxidants.

Also lignans other than hydroxymatairesinol have powerful antioxidant and anti-inflammatory potential. The antioxidant action involves all the major free radicals such as superoxide anions and peroxyl radicals (K Prasad: Antioxidant activity of secoisolariciresinol diglucoside-derived metabolites, secoisolariciresinol, enterodiol and enterolactone. Int J Angiology 9:220-225 (2000)).

According to studies, lignans may also prevent skin cancers (Thompson L. U. (1993): Potential health benefits and problems associated with antinutrients in foods. Food Res. Int. 26, 131-149).

No topical preparations, either for cosmetic or pharmaceutical use, comprising lignans, especially lignans which can be derived from wood in great quantities, or lignans or lignan derivatives, such as phenolic esters, manufactured from such wood-derivable lignans, have been described in the art.

SUMMARY OF THE INVENTION

One object of the present invention is to provide topical formulations comprising lignans or esters thereof as active ingredients, either for cosmetic or pharmaceutical use.

Another object is to provide topical formulations comprising lignans or esters thereof, active as preservatives or stabilizers for other active ingredients and/or vehicle components, wherein said formulations are useful either as cosmetics or pharmaceuticals.

Thus, the present invention concerns a topical formulation comprising an active agent, which is a lignan or a lignan ester, in a dermatologically acceptable vehicle, wherein the active agent is i) a lignan selected from the group consisting of hydroxymatairesinol, lariciresinol, secoisolariciresinol, isolariciresinol, oxomatairesinol, alpha-conidendrin, liovil, picearesinol, syringaresinol or nortrachelogenin, or ii) a lignan ester of formula (I)

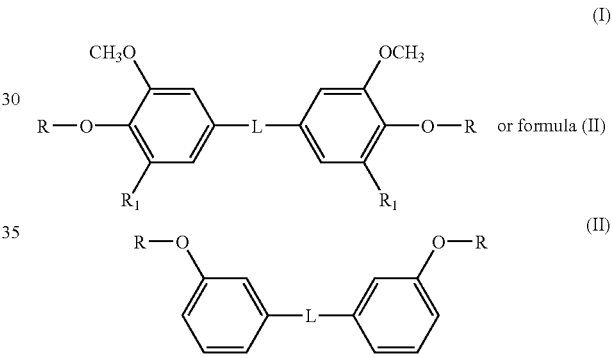

wherein L is a lignan skeleton, which optionally includes a bridge forming a ring with one of the phenyl groups in the formulae, and L in formula (I) is a lignan skeleton of any of the lignans hydroxymatairesinol, matairesinol, lariciresinol, secoisolariciresinol, isolariciresinol, oxomatairesinol, alpha-conidendrin, pinoresinol, liovil, picearesinol, arctigenin, syringaresinol or nortrachelogenin and L in formula (II) is a lignan skeleton of enterodiol or enterolactone;

$R_1$ is H or methoxy;

R is methyl, R'—CO— or R'—SO$_2$— in both of the phenyl groups in (I) and (II) or R is H in one of the phenyl groups in (I) or (II) and methyl, R'—CO— or R'—SO$_2$— in the other phenyl group;

wherein

R' is a $C_1$ to $C_{22}$ alkyl, alkenyl, arylalkyl, aralkenyl, or an aromatic group, and R' is unsubstituted or substituted with one or more hydroxy groups and/or one or more carboxyl groups, an oxo group or an amino group, or a geometric isomer or a stereoisomer thereof, provided that R is methyl only in a single R—O— substituent in a compound of formula (I) where L is a skeleton of the lignan arctigenin, and R is other than acetyl or propionyl if the lignan ester is a compound of formula (II).

DETAILED DESCRIPTION OF THE INVENTION

Definitions:

A "topical formulation" refers to a composition intended to be directly laid onto or spread on the surface of skin.

A "dermatologically acceptable vehicle" refers to excipients that are suitable for use in direct contact with human tissues without undue adverse effects or toxicity, and that further is compatible with other components in the formulation. Good aesthetic properties are also needed when said formulation is intended for cosmetic purposes.

"Esters" of lignans shall mean phenolic esters, where at least one, but preferably both of the hydroxy groups in the phenols are esterified. Furthermore, the esters also include compounds where hydroxy substituents in the lignan skeleton are esterified, in addition to the esterified hydroxy groups(s) in the phenol groups. Certain phenolic lignan esters are known in the art, namely the dibenzoate and the p-nitrodibenzoate of matairesinol; enterolactone diacetate; monoacetate, triacetate, p-hydroxymonobenzoate, and p-hydroxy-m-methoxymonobenzoate of hydroxymatairesinol; and tetraacetate and tetrabenzoate of secoisolariciresinol. Other phenolic diesters of lignans defined by formulas (I) or (II) have recently been disclosed in a patent application, PCT/FI03/00041. The international patent publication WO 00/13661 discloses i.a. the lignans enterodiol, enterolactone and matairesinol as useful ingredients in topical preparations. The patent publications EP 38600 and EP 43150 disclose acetyl esters of enterolactone and enterodiol, and propionyl esters of enterodiol as useful ingredients in topical formulations.

The terms "lignans" and "lignan esters" shall also be understood to cover their glucosides.

Preferred Lignans and Lignan Esters:

As can be seen in Scheme 1, lignans bear typically two phenyl groups, which in turn are substituted with at least a hydroxy group. An exception is the lignan arctigenin in which one of the phenolic hydroxyl groups is replaced by methoxy. Most of the lignans of formula (I) have disubstituted phenyl groups, i.e. $R_1$ is H. An exception is the rye lignan syringaresinol in which $R_1$ is methoxy. The lignan skeleton L in the formulae (I) and (II) stands for the part of the lignan molecule bearing such phenyl groups. In certain lignans such as isolariciresinol and conidendrin, the skeleton L includes a bridge which forms a ring with one of the phenyl groups in the formulae. As further can be seen, many of the lignans have also one or more hydroxy groups in the skeleton L.

The lignans or esters thereof can either be derived from natural sources, such as flaxseed, rye etc., or from wood, especially coniferous wood. Alternatively, the lignans or derivatives can be manufactured synthetically or by use of microbiological methods.

Especially preferred lignans are hydroxymatairesinol, lariciresinol, secoisolariciresinol and isolariciresinol and their geometric isomers and stereoisomers.

Particularly preferred lignan esters are esters of the lignans according to formula (I) which are hydroxymatairesinol, matairesinol, lariciresinol, secoisolariciresinol, isolariciresinol, oxomatairesinol, alpha-conidendrin, pinoresinol, liovil, picearesinol, arctigenin, syringaresinol or nortrachelogenin, or lignans of formula (II), which are enterolactone or enterodiol.

The ester is preferable a phenolic ester, more preferable a phenolic diester. Especially preferable are phenolic esters where the ester groups are the same.

Preferable diphenolic esters are, for example, esters of mono- or dicarboxylic fatty acids, hydroxy acids and sulfonic acids. As examples of suitable dicarboxylic acid esters can be mentioned succinates, glutarates, and malonic acid esters. Lactic acid esters are examples of esters with hydroxysubstituted acids. Tartaric acid and citric acid esters are examples of esters of acids with several carboxylic groups and one or more hydroxy groups.

Particularly preferable lignan esters to be added into topical formulations are aliphatic fatty acid diesters of lignans. Such lignan esters may be superior with regard to miscibility and dissolution into fat-based ointments. Furthermore, as more lipid soluble substances, their skin penetration is likely to be enhanced thus resulting in better penetration into epidermal and dermal layers of the skin. This is essential for compounds which are expected to result in anti-aging effects, such as antioxidants.

Activity of the Lignans or Lignan Derivatives:

The lignans or lignan esters may be useful as active agents in topical preparations, either cosmetic or pharmaceutical preparations, especially as anti-aging substances for treating signs of dermatological aging, both photoaging and intrinsic aging, including skin wrinkles such as fine wrinkling in the eye area or "crows feet" or fine wrinkles around the mouth area, irregular pigmentation, sallowness, loss of skin resilience and elasticity.

The lignans or esters thereof may also be useful as anti-inflammatory agents or as skin cancer preventing agents.

The following table shows the antioxidant effect of lignans or their esters using an in vitro model for inhibition of lipid peroxidation. In this model, lignan compounds were compared to the well known, potent antioxidant Trolox, which is a water-soluble derivative of vitamin E.

| Test compound: | Inhibition of lipid peroxidation[1]: |
| --- | --- |
| Hydroxymatairesinol (HMR) | 0.06 |
| Lariciresinol | 0.07 |
| Secoisolariciresinol | 0.09 |
| α-Conidendrin | 0.067 |
| Matairesinol | 0.054 |
| Nortrachelogenin | 0.15 |
| Oxomatairesinol | 0.11 |
| Matairesinoibutyrate | 0.35 |
| HMR-butyrate | 0.1 |
| HMR-benzoate | 0.12 |
| Trolox | 0.22 |

[1]Peroxidation of microsomal lipids initiated by tert-butylhydroperoxide, detection of peroxidation by chemiluminescence (Ahotupa M et al., Clin biochem, 29: 139-144, 1996). Results are given as IC50-values (that is, concentration of test material that inhibits lipid peroxidation by 50%); μmol/L.

Lignans or their esters may also due to their antioxidant activity be useful in preventing other unstable, easily oxidized constituents of topical compositions from being auto-oxidized. Such easily oxidized components include for example omega-3 and omega-6 series fatty acids and other fats typically present in e.g. liposomal formulations.

When used in combination with a dermatologically acceptable vehicle to form a topical formulation, the effective amount of the lignan or lignan ester can be within the range from about 0.01% to about 50%, preferably 0.01% to 20%. Both the effective amount and the frequency of application will vary within this range based on the particular skin condition treated, the age and physical condition of the person under treatment, the severity of the condition, the duration of treatment, the nature of concurrent treatments, the specific agent or agents employed, the particular vehicle utilized to deliver the agent or agents, and other like factors within the knowledge and expertise of those skilled in the art.

Preferred Formulations:

The topical formulation according to this invention can be a liquid formulation, a semisolid formulation or a foam, shampoo, spray, patch, stick, batch additive or a sponge. Preferable formulations are liquid or semi-solid formulations.

Preferable liquid formulations for topical use are preparations of a variety of viscosities intended to be applied to the skin or nails in order to obtain a local action or transdermal activity. They are solutions, emulsions, micro-emulsions, lotions or suspensions which may contain one or more active substances in a suitable vehicle. They may be, for example, in the form of aqueous, aqueous/alcoholic or oily solutions; dispersions of the lotion or serum type, emulsions obtained by dispersion of a fatty phase in an aqueous phase (oil-in-water) or conversely (water-in-oil). They may also contain additional suitable antimicrobial preservatives and antioxidants as well as other excipients such as stabiliser, emulsifiers and thickeners.

Semi-solid formulations for topical use are intended for local or transdermal delivery of active substance, or for their emollient or protective action. The preparations consist of a simple or compound basis in which, usually, one or more active substances are dissolved or dispersed. According to its composition, the basis may influence the activity of the preparation. Preparations may contain suitable excipients such as antimicrobial preservatives, antioxidants, stabilisers, emulsifiers, thickeners and penetration enhancers. Several categories of semi-solid preparations for topical application may be distinguished: creams, gels, ointments, pastes and poultices.

While lotions or creams can be made using conventional homogenization methods known to those skilled in the art, it is also possible to use a process of microfluidization that involves co-mixing the aqueous phase and the oil phase of such creams and lotions in a high-pressure homogenizer that reduces the emulsion particle size dramatically to about 1/400 of the size of those in creams and lotions prepared without applying high pressure. Microfluidization allows one to prepare elegant stable creams and lotions containing effective amounts of a lignan or lignan ester without the use of traditional emulsifiers and surfactants.

The inventive compositions can also be in the form of a multiphase emulsion, such as a water-in-oil-in-water type emulsion as disclosed in U.S. Pat. No. 4,254,105, or oil-in-water-in silicone.

The formulations according to this invention can also be made as a liposomal formulation, for example, according to the methods described in Mezei, J. Pharmaceut. Pharmacol., vol. 34, pp. 473-474 (1982), or modification thereof. In such compositions, droplets of the lignan or lignan ester solution or suspension can be entrapped inside the liposomal vesicles with the shell of the liposome being a phospholipid or other suitable lipids (e.g. skin lipids). To form a topical composition, the liposomes can then be added to any carrier system described above according, for example, to the preparation modes, uses and compositions of topical liposomes described in Mezei, Topics in Pharmaceutical Sciences, Breimer et al. Eds., pp. 345-358, Elsevier Science Publishers BV, N.Y. (1985), or according to the reverse-phase evaporation method described in Szoka et al., Proc. Nat. Acad. Sciences, vol. 75, pp. 4194-4198 (1978), and Diploses et al., J. Soc. Cosmetic Chemists, vol. 43, pp. 93-100 (1992). Lignans or lignan esters can also be entrapped in complexing agents, such as cyclodextrins, or polymeric vesicles with a shell consisting of a suitable polymeric material, such as gelatin, cross-linked gelatin, polyamide, poylacrylates and the like, to form a vesicle that is then incorporated into the topical formulation.

Preferred Vehicle Components:

The aim of the vehicles is to facilitate the distribution of the composition when applied to the skin. Vehicles other than or in addition to water can include liquid or solid emollients, solvents, emulsifiers, humectants, thickeners, powders, surfactants, moisturizers, exfolients, stabilizers, preservatives, lubricants, chelating agents, skin penetration enhancers, fillers, fragrances, perfumes, odor absorbers, colorants and opacifiers.

According to a preferable embodiment, the lignan or lignan ester is in the form of an inclusion complex with a cyclodextrin.

Suitable emollients include, for example mineral oil, petrolatum, paraffin, ceresin, ozokerite, microcystraline wax, perhydrosqualene dimethyl polysiloxanes, methylphenyl polysiloxanes, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in Sagarin, Cosmetics, Science and Technology, 2nd Ed., vol. 1, pp. 32-43 (1972).

The emulsifiers can be cationic, anionic, nonionic, amphoteric, or a combination thereof. Nonionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isothionates. Other suitable emulsifiers can be found in McCutcheon, Detergents and Emulsifiers, North American Edition, pp. 317-324 (1986).

The preservatives suitable for use with the present formulations include alkanols, especially ethanol and benzyl alcohol, parabens, sorbates, urea derivatves, and isothiazolinones.

Examples of suitable thickening agents include xanthan gum, xanthan gum brine tolerant, hydroxypropyl cellulose, hydroxyethyl cellulose, carbopol and gum acacia, Sepigel 305 (available from Seppic Co., France), vee-gum or magnesium aluminum silicate.

As examples of suitable humectants can be mentioned urea, PCA, amino acids, certain polyols and other compounds with hygroscopic properties.

Other Possible Active Ingredients:

The topical formulation according to the present invention may include a lignan or lignan ester or their mixture as the only active ingredients.

Alternatively, the lignan or lignan ester or their mixture can also be used in combination with other active agents. Suitable other active agents include, but are not limited to, antiseptics, antifungals, bactericides, vitamins, sunscreens, retinoids, antiallergenic agents, depigmenting agents, anti-inflammatory agents, hormones and anesthetics.

The role of the lignan or lignan ester in these formulations may be to provide a synergistic effect in combination with the other active ingredient(s), i.e. an antioxidant, anti-inflammatory or skin cancer preventing effect. Alternatively, the role may be to mainly serve as preservative or stabilizer for the other active agent(s) and/or vehicles.

Particularly Suitable Vehicles in the Formulations:

a) Creams:
- Water-in-oil emulsifying agents such as wool alcohols, sorbitan esters and monoglycerides.
- Oil-in-water emulsifying agents such as sulphate fatty alcohols, sodium soaps, polysorbates, polyoxyl fatty acid and fatty alcohol esters.

b) Gels:
- Lipophilic gels usually consist of liquid paraffin with polyethylene or fatty oils gelled with colloidal silica or aluminium soaps.
- Hydrophilic gels consist of water, glycerol or propylene glycol gelled with suitable gelling agents such as starch, cellulose derivates, carbomers, and magnesium-aluminium silicates.

c) Ointments:
- Ointments consist of a single phase basis in which solids or liquid may be dispersed.
- Hydrophopic ointments; typical bases used for formulations are hard, liquid and light liquid paraffines, vegetable oils, animal fats, synthetic glycerides, waxes and liquid polyalkylsiloxanes.
- Water-emulsifying ointments; emulsifiers: wool alcohols, Sorbian esters, monoglycerides and fatty alcohols, sulphate fatty alcohols, polysorbates, macrogol cetostearyl ether or esters of fatty acids with macrogols.
- Hydrophilic ointments; mixtures of liquid and solid macrogols The invention will be illuminated by the following non-restrictive Examples.

EXAMPLES

The following formulations are examples of especially preferred topical formulations:

Example 1

Water-in-Oil Emulsion

| | |
|---|---|
| Active substance (hydroxymatairesinol, matairesinoldibutyrate) | 0.01-20% |
| Emulsifying agent[1] | 1-25% |
| Humectant[2] | 5-80% |
| Preservative[3] | 0.01-0.5% |
| Water | 20-50% |

[1]such as sorbitan fatty acid esters (e.g. sorbitan sesquioleate, sorbitan monostearate, sorbitan mono-oleate, sorbitan trioleate, sorbitan tristearate, sorbitan monolaurate, sorbitan monopalmitate), wool alcohols and monoglycerides
[2]such as glycerin, propylene glycol
[3]such as methylparaben, ethylparaben, propylparaben, sorbic acid Example 2

Oil-in Water Emulsion

| | |
|---|---|
| Active substance (hydroxymatairesinol, matairesinoldibutyrate) | 0.01-20% |
| Emulsifying agent[1] | 1-25% |
| Humectant[2] | 5-80% |
| Preservative[3] | 0.01-0.5% |
| Water | 20-50% |

[1]such as sulphate fatty alcohols, sodium soaps, polysorbates, polyoxyl fatty acids and fatty alcohol esters
[2]such as glycerin, propylene glycol
[3]such as methylparaben, ethylparaben, propylparaben, sorbic acid Example 3

Gel

| | |
|---|---|
| Active substance (hydroxymatairesinol, matairesinoldibutyrate) | 0.01-1% |
| Gelling agent[1] | 0.5-6% |
| Solvent[2] | 10-45% |
| Preservative[3] | |
| Water | 20-50% |

[1]such as starch, cellulose derivatives, carbomers and magnesium-aluminium silicates
[2]such as ethanol, isopropanol
[3]such as methylparaben, ethylparaben, propylparaben, sorbic acid Example 4

Ointment

| | |
|---|---|
| Active substance (hydroxymatairesinol, matairesinoldibutyrate) | 0.01-20% |
| Ointment base[1] | 1-25% |
| Preservative[2] | 0.01-0.5% |

[1]such as liquid paraffines, vegetable oils, animal fats, synthetic glycerides, macrogols
[2]such as methylparaben, ethylparaben, propylparaben, sorbic acid Example 5

Oil-in-Water Emulsion

| | |
|---|---|
| Active substance (hydroxymatairesinol, matairesinoldibutyrate) | 1.0% |
| Cetostearyl alcohol | 25.0% |
| Glycerin | 4.0% |
| Glycerylmonostearate | 4.8% |
| Methylparaben | 0.1% |
| Propylparaben | 0.1% |
| Water | 65.0% |

Example 6

Water-in-Oil Emulsion

| | |
|---|---|
| Active substance (hydroxymatairesinol, matairesinoldibutyrate) | 1.0% |
| Stearyl alcohol | 35.0% |
| Macrogol stearate | 8.0% |
| Propylene glycol | 10.0% |
| Mineral oil | 5.0% |
| Methylparaben | 0.1% |
| Propylparaben | 0.1% |
| Water | 40.8% |

Example 7

Ointment

| | |
|---|---|
| Active substance (hydroxymatairesinol, matairesinoldibutyrate) | 1.0% |
| Petrolatum | 63.8% |
| Paraffinum liquidum | 15.0% |
| Glyceryl stearate | 10.0% |
| Propylene glycol | 10.0% |
| Sorbic acid | 0.2% |

Example 8

Gel

| | |
|---|---|
| Active substance (hydroxymatairesinol, matairesinoldibutyrate) | 0.1% |
| Carbomer | 3.0% |
| Glycerin | 10.0% |
| Ethanol | 33.9% |
| Water | 53.0% |

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

Scheme 1

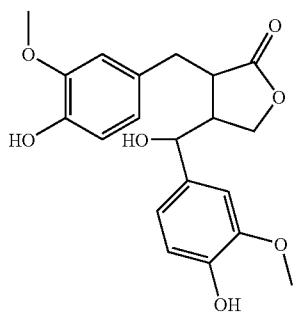

Hydroxymatairesinol

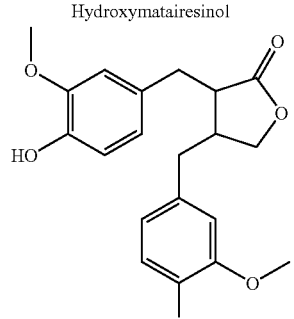

Matairesinol

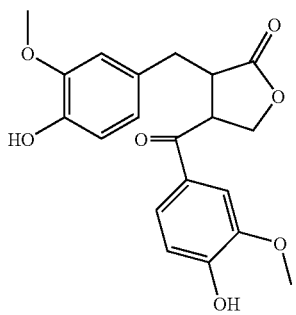

Oxomatairesinol

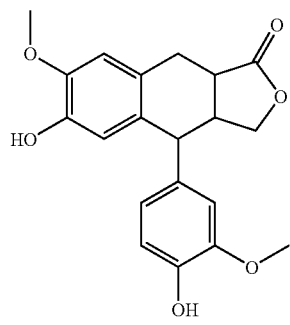

Conidendrin

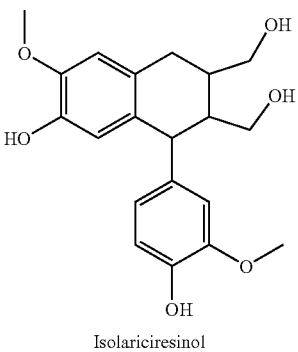

Isolariciresinol

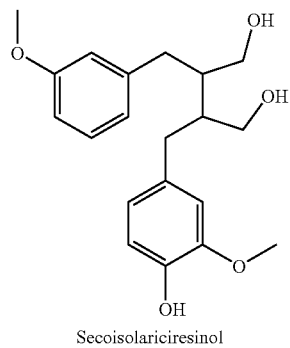

Secoisolariciresinol

-continued

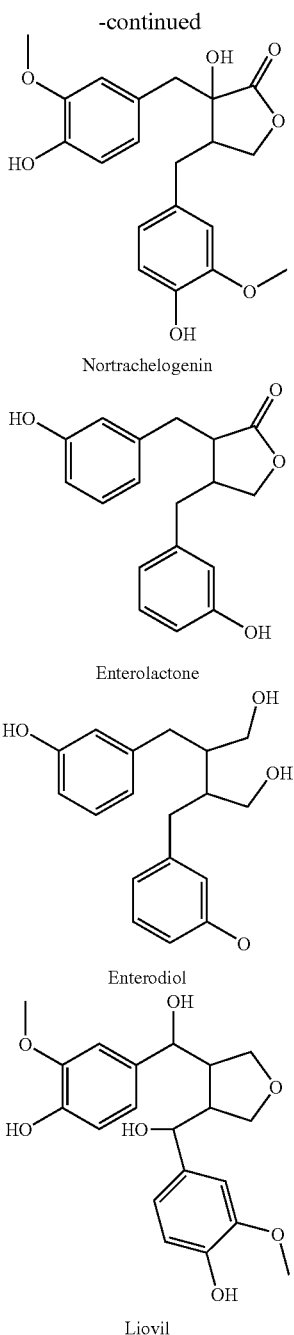

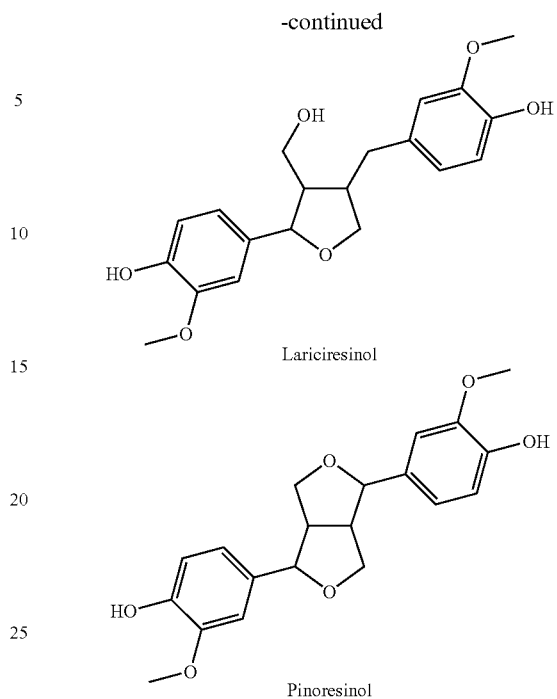

The invention claimed is:

1. A method for treating dermatological aging, comprising applying onto the skin of a patient suffering from dermatologic aging a cosmetic topical formulation comprising an active agent selected from the group consisting of hydroxymatairesinol, a geometric isomer thereof and a stereoisomer of hydroxymatairesinol, in a dermatologically acceptable vehicle, wherein the formulation is a) a liquid formulation selected from the group consisting of emulsions, microemulsions, lotions, suspensions and solutions;

b) a semisolid formulation; or c) a foam, shampoo, spray, patch, stick or a sponge.

2. The method according to claim 1, wherein the liquid formulation is a suspension, lotion or emulsion.

3. The formulation according to claim 1, wherein the semisolid formulation is a cream, gel, ointment, paste or poultice.

* * * * *